United States Patent [19]
Büyüktimkin et al.

[11] Patent Number: 6,046,244
[45] Date of Patent: Apr. 4, 2000

[54] TOPICAL COMPOSITIONS FOR PROSTAGLANDIN $E_1$ DELIVERY

[75] Inventors: Servet Büyüktimkin; Nadir Büyüktimkin, both of Lawrence, Kans.; James Yeager, Deerfield, Ill.

[73] Assignee: Nexmed Holdings, Inc., Robbinsville, N.J.

[21] Appl. No.: 08/964,509

[22] Filed: Nov. 5, 1997

[51] Int. Cl.[7] .......................... A61K 47/14; A61K 47/18; A61K 9/06
[52] U.S. Cl. .......................... 514/785; 514/946; 514/947; 514/573
[58] Field of Search .................... 514/573, 946, 514/947, 785; 560/121

[56] References Cited

U.S. PATENT DOCUMENTS

| | | | |
|---|---|---|---|
| 4,661,524 | 4/1987 | Thomson et al. | 514/682 |
| 4,731,241 | 3/1988 | Yamada et al. | 514/236.2 |
| 4,732,892 | 3/1988 | Sarpotdar et al. | 514/178 |
| 4,771,004 | 9/1988 | Higuchi | 436/5 |
| 4,808,414 | 2/1989 | Peck et al. | 424/449 |
| 4,865,848 | 9/1989 | Cheng et al. | 424/449 |
| 4,973,468 | 11/1990 | Chiang et al. | 424/449 |
| 4,980,378 | 12/1990 | Wong et al. | 514/785 |
| 5,082,866 | 1/1992 | Wong et al. | 514/785 |
| 5,413,794 | 5/1995 | Suzuki et al. | 424/449 |
| 5,534,260 | 7/1996 | Petersen et al. | 424/448 |
| 5,534,554 | 7/1996 | Katz et al. | 514/724 |

OTHER PUBLICATIONS

Uekama et al. Improved Transdermal delivery of Prostaglandin E1 Through Hairless Mouse Skin: Combined Use of Carboxymethyl–ethyl–beta–cyclodextrin and Penetration Enhancers.
Journal of Pharmaceutical Pharmacology. Feb. 1992. vol. 44, No. 2. pp. 119–121.
Adachi et al. Inhibitory Effect of Prostaglandin E1 on Laurate–Induced Peripheral Vascular Occlusive Sequelae in Rabbits: Optimized Topical Formulation with Beta–Cyclodextrin Derivative And Penetration Enhancer HPE–101.
Journal of Pharmaceutical Pharmacology. Dec. 1992. vol. 44, No. 12. pp. 1033–1035.
Article, "Alkyl N,N–Disubstituted–Amino Acetates", Büyüktimkin, N., et al., pp. 91–102, appearing in "Percutaneous Penetration Enhancers," 1995 by CRC Press, Inc.

*Primary Examiner*—Robert H. Harrison
*Attorney, Agent, or Firm*—Olson & Hierl, Ltd.

[57] ABSTRACT

A topical composition of a semi-solid consistency suitable is provided for transdermal application of prostaglandin $E_1$. The composition comprises prostaglandin $E_1$, a penetration enhancer, a polysaccharide gum, a lipophilic compound, and an acidic buffer system. The penetration enhancer is an alkyl-2-(N,N-disubstituted amino)-alkanoate ester, an (N,N-disubstituted amino)-alkanol alkanoate, or a mixture of these. The lipophilic compound may be an aliphatic $C_1$ to $C_8$ alcohol, an aliphatic $C_8$ to $C_{30}$ ester, or a mixture of these. The composition includes a buffer system capable of providing a buffered pH value for said composition in the range of about 3 to about 7.4.

27 Claims, 2 Drawing Sheets

TOPICAL COMPOSITIONS FOR PROSTAGLANDIN $E_1$ DELIVERY

TECHNICAL FIELD OF THE INVENTION

This invention relates to pharmaceutical compositions for transdermal administration of prostaglandin drugs to a patient.

BACKGROUND OF THE INVENTION

Prostaglandin $E_1$ is a derivative of prostanoic acid, a 20-carbon atom lipid acid, represented by the formula:

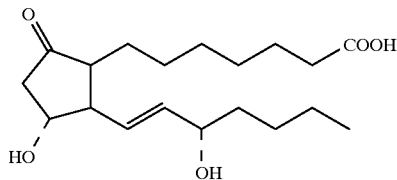

and is commercially available, e.g., from Chinoin Pharmaceutical and Chemical Works Ltd. (Budapest, Hungary) under the designation "Alprostadil USP" and from The Upjohn Company (Kalamazoo, Mich.) under the designation "Prostin VR."

Prostaglandin $E_1$ is a vasodilator useful to maintain open blood vessels and therefore, to treat peripheral vascular disease among other ailments. While the potential benefits from transdermal delivery of prostaglandin $E_1$ have long been recognized, prior efforts at developing a topical composition for prostaglandin delivery have not been fully successful.

In particular, there is presently no commercial source for a topical semi-solid formulation that is useful without a supporting device such as a patch, adhesive strip, and the like. For example, U.S. Pat. No. 5,380,760 to Wendel et al. is directed to a topical prostaglandin formulation that includes a pressure-sensitive, adhesive sheet of polyisobutylene.

Working alone most drugs, prostaglandin formulations included, do not sufficiently permeate the skin to provide drug concentration levels comparable to those obtained from other drug delivery routes. To overcome this problem, topical drug formulations typically include a skin penetration enhancer. Skin penetration enhancers also may be referred to as absorption enhancers, accelerants, adjuvants, solubilizers, sorption promoters, etc. Whatever the name, such agents serve to improve drug absorption across the skin. Ideal penetration enhancers not only increase drug flux across the skin, but do so without irritating, sensitizing, or damaging skin. Furthermore, ideal penetration enhancers should not affect available dosage forms (e.g. cream or gel), or cosmetic quality of the topical composition.

A wide variety of compounds have been evaluated as to their effectiveness in enhancing the rate of penetration of drugs through the skin. See, for example, *Percutaneous Penetration Enhancers,* Maibach H. I. and Smith H. E. (eds.), CRC Press, Inc., Boca Raton, Fla. (1995), which surveys the use and testing of various skin penetration enhancers, and Büyüktimkin et al., Chemical Means of Transdermal Drug Permeation Enhancement in *Transdermal and Topical Drug Delivery Systems,* Gosh T. K., Pfister W. R., Yum S. I. (Eds.), Interpharm Press Inc., Buffalo Grove, Ill. (1997).

A fully successful formulation for prostaglandin $E_1$ has not yet been identified. Unfortunately, prostaglandin $E_1$ is readily transformed by rearrangement and other reactions. This relative instability tends to complicate efforts at formulating composition for transdermal delivery.

The present invention addresses these problems by providing a semi-solid, separation resistant composition for relatively rapid, sustained delivery of prostaglandin $E_1$.

SUMMARY OF THE INVENTION

A pharmaceutical composition suitable for topical application comprises prostaglandin $E_1$, a penetration enhancer, a polysaccharide gum, a lipophilic compound, and an acidic buffer system. The penetration enhancer is an alkyl-2-(N,N-disubstituted amino)-alkanoate ester, an (N,N-disubstituted amino)-alkanol alkanoate, or a mixture of these. The lipophilic compound may be an aliphatic $C_1$ to $C_8$ alcohol, an aliphatic $C_8$ to $C_{30}$ ester, or a mixture of these. The composition includes a buffer system capable of providing a buffered pH value for said composition in the range of about 3 to about 7.4. If desired, stabilizers and emulsifiers may be included.

Compositions of the present invention can take the form of a semi-solid suitable for topical application. In use as a topical agent, these compositions exhibit relatively high prostaglandin penetration and bioavailability without requiring a wasteful overloading prostaglandin concentration. The composition further exhibit reduced skin irritation, sensitivity and damage.

Other and further aims, purposes, features, advantages, embodiments and the like will be apparent to those skilled in the art from the present specification and the appended claims.

DETAILED DESCRIPTION OF THE INVENTION

Figure 1:
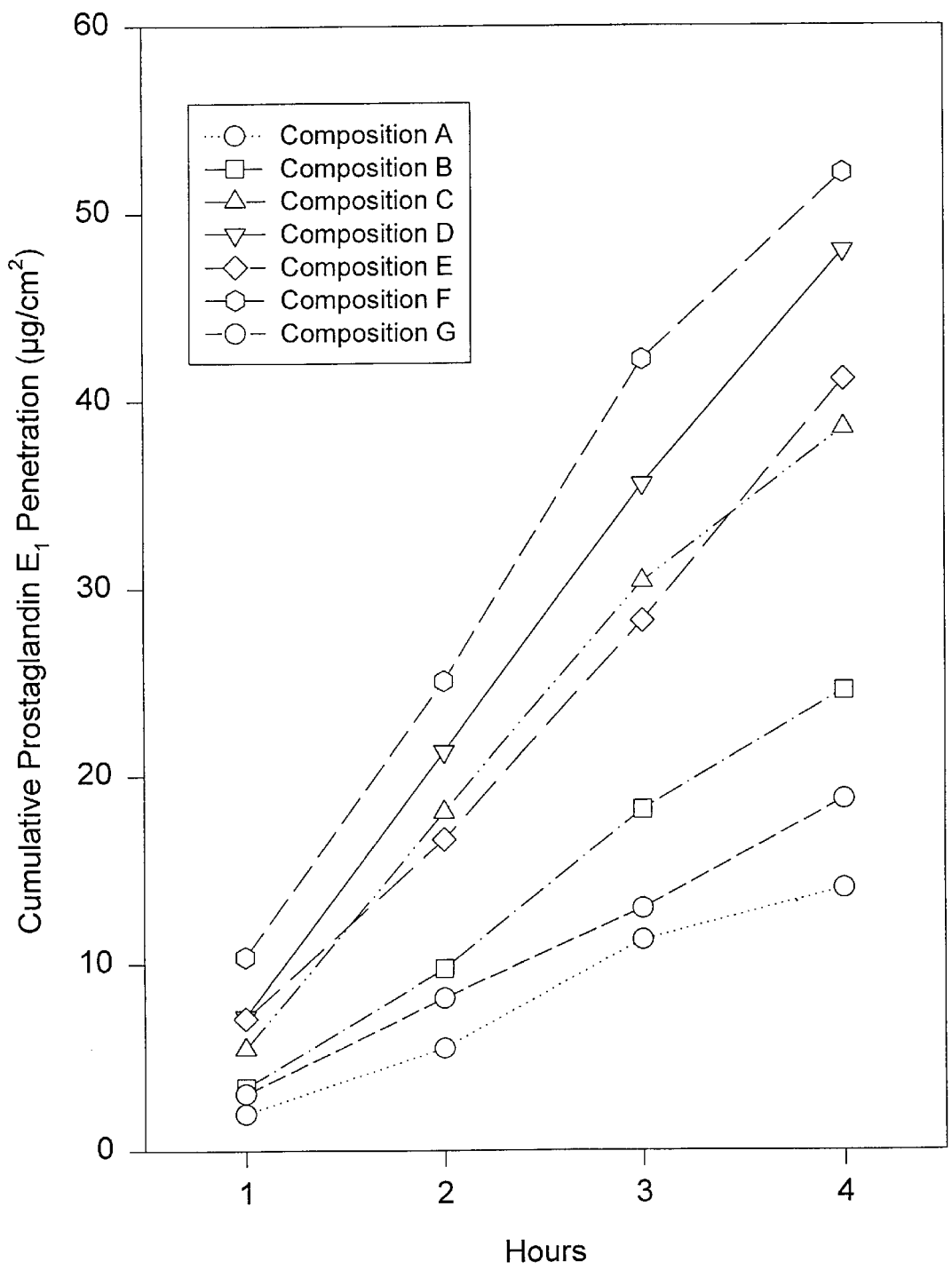
FIG. 1 is a graph of the cumulative prostaglandin $E_1$ penetration through shed snake skin of seven prostaglandin $E_1$ compositions prepared according to the present invention.
Figure 2:
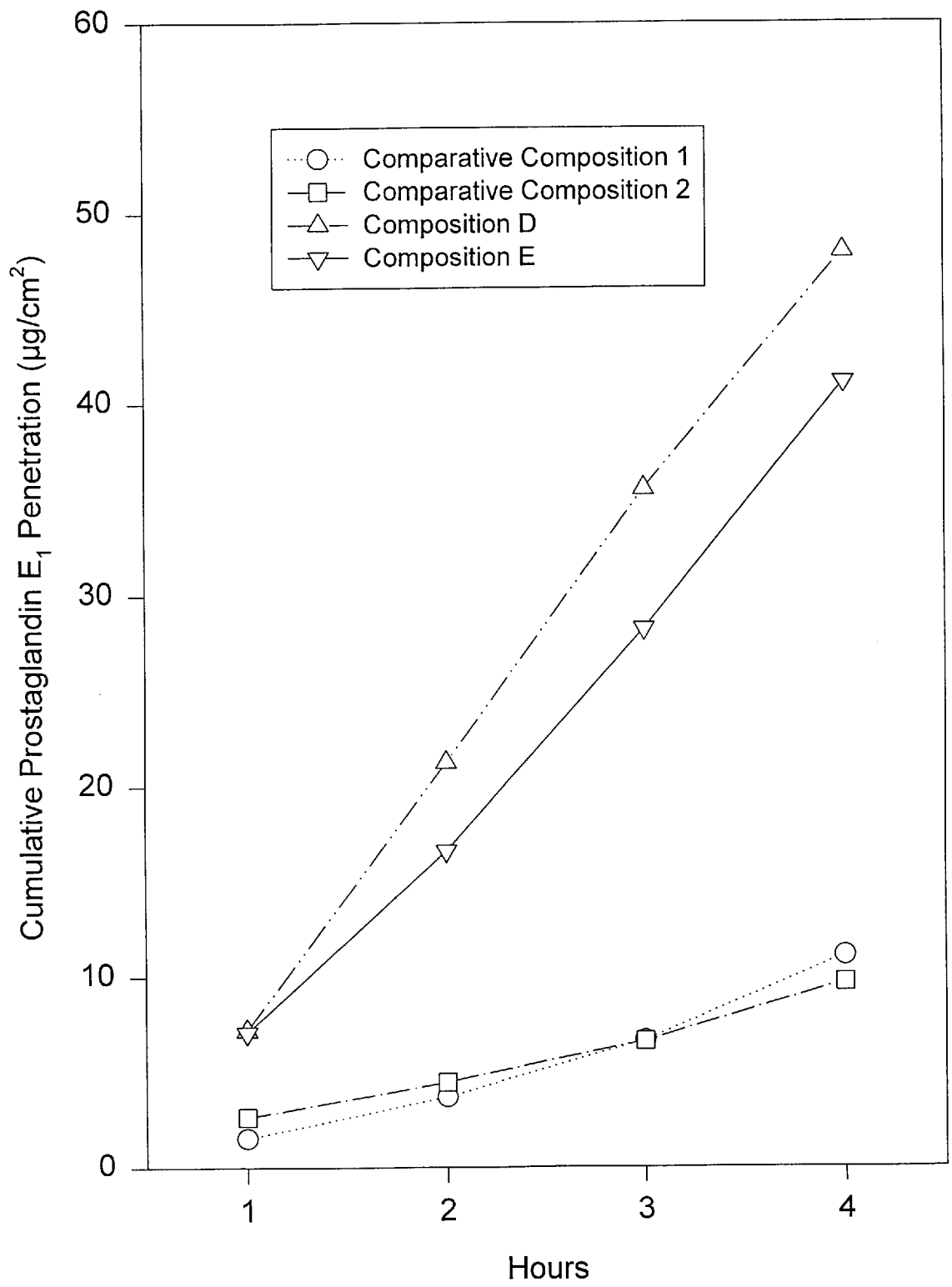
FIG. 2 is a comparison graph of the cumulative prostaglandin $E_1$ penetration through shed snake skin of two prostaglandin $E_1$ compositions prepared according to the present invention and two comparative compositions.

The pharmaceutical composition of the present invention comprises prostaglandin $E_1$, an alkyl (N,N-disubstituted amino) ester, a polysaccharide gum, a lipophilic compound, and an acid buffer system.

Prostaglandin $E_1$ is well known to those skilled in the art. Reference may be had to various literature references for its pharmacological activities, side effects, and normal dosage ranges. See for example, *Physician's Desk Reference,* 51st Ed. (1997), *The Merck Index,* 12th Ed., Merck & Co., New Jersey (1996), and *Martindale The Extra Pharmacopoeia,* 28th Ed., London, The Pharmaceutical Press (1982). Prostaglandin $E_1$ as well as other compounds referenced herein are intended to encompass pharmaceutically acceptable derivatives including physiologically compatible salts and ester derivatives thereof.

The quantity of prostaglandin $E_1$ in the pharmaceutical compositions of the present invention is a therapeutically effective amount and necessarily varies according to the desired dose, the dosage form (e.g., suppository or topical), and the particular form of prostaglandin $E_1$ used. The composition generally contains between 0.1 percent to 1 percent prostaglandin $E_1$, preferably from 0.3 percent to 0.5 percent, based on the total weight of the composition.

An important component of the present invention is the penetration enhancer. The penetration enhancer is an alkyl-2-(N,N-disubstituted amino)-alkanoate, an (N,N-disubstituted amino)-alkanol alkanoate, or a mixture of these. For convenient reference, alkyl-2-(N,N-disubstituted amino)-alkanoates and (N,N-disubstituted amino)-alkanol alkanoates can be grouped together under the label alkyl (N,N-disubstituted amino) esters.

Alkyl-2-(N,N-disubstituted amino)-alkanoates suitable for the present invention can be represented as follows:

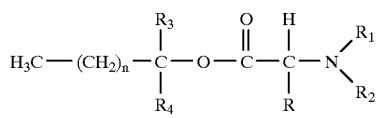

wherein n is an integer having a value in the range of about 4 to about 18; R is a member of the group consisting of hydrogen, $C_1$ to $C_7$ alkyl, benzyl and phenyl; $R_1$ and $R_2$ are members of the group consisting of hydrogen and $C_1$ to $C_7$ alkyl; and $R_3$ and $R_4$ are members of the group consisting of hydrogen, methyl and ethyl.

Preferred alkyl (N,N-disubstituted amino)-alkanoates are $C_4$ to $C_{18}$ alkyl (N,N-disubstituted amino)-acetates and $C_4$ to $C_{18}$ alkyl (N,N-disubstituted amino)-propionates. Exemplary specific alkyl-2-(N,N-disubstituted amino)-alkanoates include dodecyl 2-(N,N dimethylamino)-propionate (DDAIP);

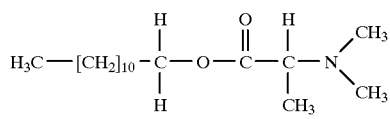

and dodecyl 2-(N,N-dimethylamino)-acetate (DDAA);

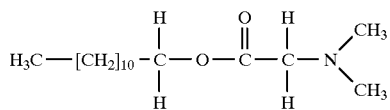

Alkyl-2-(N,N-disubstituted amino)-alkanoates are known. For example, dodecyl 2-(N,N-dimethylamino)-propionate (DDAIP) is available from Steroids, Ltd. (Chicago, Ill.). In addition, alkyl-2-(N,N-disubstituted amino)-alkanoates can be synthesized from more readily available compounds as described in U.S. Pat. No. 4,980,378 to Wong et al., which is incorporated herein by reference to the extent that it is not inconsistent. As described therein, alkyl-2-(N,N-disubstituted amino)-alkanoates are readily prepared via a two-step synthesis. In the first step, long chain alkyl chloroacetates are prepared by reaction of the corresponding long chain alkanols with chloromethyl chloroformate or the like in the presence of an appropriate base such as triethylamine, typically in a suitable solvent such as chloroform. The reaction can be depicted as follows:

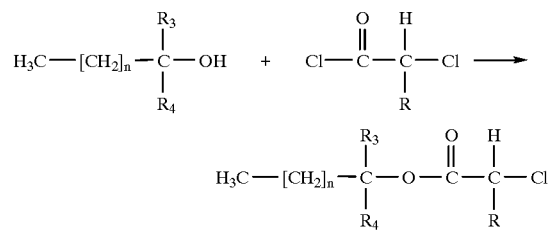

wherein R, $R_3$, $R_4$ and n are defined as above. The reaction temperature may be selected from about 10° C. to about 200° C. or reflux, with room temperature being preferred. The use of a solvent is optional. If a solvent is used, a wide variety of organic solvents may be selected. Choice of a base is likewise not critical. Preferred bases include tertiary amines such as triethylamine, pyridine and the like. Reaction time generally extends from about one hour to three days.

In the second step, the long chain alkyl chloroacetate is condensed with an appropriate amine according to the scheme:

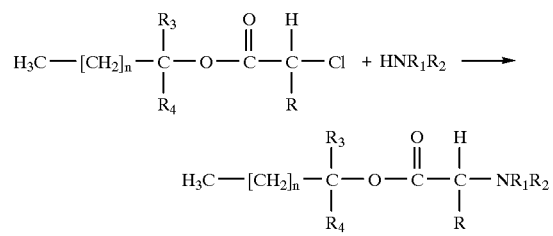

wherein n, R, $R_1$, $R_2$, $R_3$ and $R_4$ are defined as before. Excess amine reactant is typically used as the base and the reaction is conveniently conducted in a suitable solvent such as ether. This second step is preferably run at room temperature, although temperature may vary. Reaction time usually varies from about one hour to several days. Conventional purification techniques can be applied to ready the resulting ester for use in a pharmaceutical compound.

Suitable (N,N-disubstituted amino)-alkanol alkanoates can be represented by the formula:

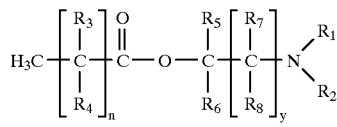

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are members of the group consisting of hydrogen, $C_1$ to $C_8$ alkyl, and $C_1$ to $C_8$ aryl; and $R_8$ is a member of the group consisting of hydrogen, hydroxyl, $C_1$ to $C_8$ alkyl, and $C_1$ to $C_8$ aryl.

Preferred (N,N-disubstituted amino)-alkanol alkanoates are $C_5$ to $C_{18}$ carboxylic acid esters. Exemplary specific (N,N-disubstituted amino)-alkanol alkanoates include 1-(N, N-dimethylamino)-2-propanol dodecanoate (DAIPD);

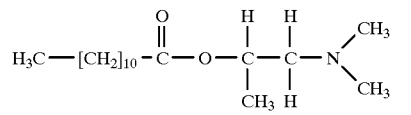

1-(N, N-dimethylamino)-2-propanol myristate (DAIPM)

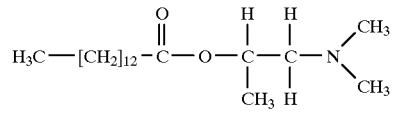

1-(N, N-dimethylamino)-2-propanol oleate (DAIPO);

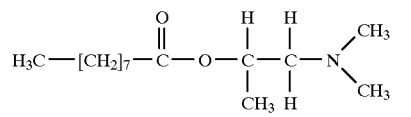

The (N,N-disubstituted amino)-alkanol alkanoates are readily prepared by reacting the corresponding aminoalkinol with lauroyl chloride in the presence of triethylamine. A solvent such as chloroform is optional but preferred. For example, 1-(N,N-dimethylamino)-2-propanol can be reacted with lauroyl chloride in chloroform and in the presence of triethylamine to form 1-(N,N-dimethylamino)-2-propanol dodecanoate (DAIPD).

Among the suitable penetration enhancers for the present invention DDAIP is generally preferred.

The penetration enhancer is present in an amount sufficient to enhance the penetration of the prostaglandin $E_1$. The specific amount varies necessarily according to the desired release rate and the specific form of prostaglandin $E_1$ used. Generally, this amount ranges from about 0.5 percent to about 10 percent, based on the total weight of the composition. Preferably, the penetration enhancer is about 5 weight percent of the composition.

Polysaccharide gums are also an important ingredient to the present composition. Suitable representative gums are those in the galactomannan gum category. A galactomannan gum is a carbohydrate polymer containing D-galactose and D-mannose units, or other derivatives of such a polymer. There is a relatively large number of galactomannans, which vary in composition depending on their origin. The galactomannan gum is characterized by a linear structure of β-D-mannopyranosyl units linked (1→6). Single membered α-D-manopyranosyl units, linked (1→6) with the main chain, are present as side branches. Galactomannan gums include guar gum, which is the pulverized endosperm of the seed of either of two leguminous plants (cyamposis tetragonalobus and psoraloids) and locust bean gum, which is found in the endosperm of the seeds of the carobtree (ceratonia siliqua). Locust bean gum is preferred for the present invention.

Other suitable representative gums include agar gum, carrageenan gum, ghatti gum, karaya gum, rhamsan gum and xanthan gum. The composition of the present invention may contain a mixture of various gums, or mixture of gums and acidic polymers.

Gums, and galactomannan gums in particular, are well-known materials. See for instance, *Industrial Gums: Polysaccharides & Their Derivatives,* Whistler R. L. and BeMiller J. N. (eds.), 3rd Ed. Academic Press (1992) and Davidson R. L., *Handbook of Water-Soluble Gums & Resins,* McGraw-Hill, Inc., New York (1980). Most gums are commercially available in various forms, commonly a powder, and ready for use in foods and topical compositions. For example, locust bean gum in powdered form is available from Tic Gums Inc. (Belcam, Md.).

The polysaccharide gums are represent in the range from about 0.5 percent to about 5 percent, based on the total weight of the composition, with the preferred range being from 0.5 percent to 2 percent. Illustrative compositions are given in the examples, below.

An optional alternative to the polysaccharide gum is a polyacrylic acid polymer. A common variety of polyacrylic acid polymer is known generically as "carbomer." Carbomer is polyacrylic acid polymers lightly cross-linked with poly-alkenyl polyether. It is commercially available from the B. F. Goodrich Company (Akron, Ohio) under the designation "CARBOPOL™." A particularly preferred variety of carbomer is that designated as "CARBOPOL 940."

Other polyacrylic acid polymers suitable for use in practicing this invention are those commercially available under the designations "Pemulen™" (B. F. Goodrich Company) and "POLYCARBOPHIL™" (A. H. Robbins, Richmond, Va.). The Pemulen™ polymers are copolymers of $C_{10}$ to $C_{30}$ alkyl acrylates and one or more monomers of acrylic acest methacrylic acid or one of their simple esters crosslinked with an allyl ether of sucrose or an allyl ether of pentaerythritol. The POLYCARBOPHIL™ enhancer is a polyacrylic acid cross-linked with divinyl glycol.

Where polyacrylic acid polymers are present, they represent about 0.5 percent to about 5 percent of the composition, based on its total weight.

Another important component of the present invention is a lipophilic compound. The term lipophilic compound as used herein refers to an agent that is both lipophilic and hydrophilic. The $C_1$ to $C_8$ aliphatic alcohols, the $C_2$ to $C_{30}$ aliphatic esters, and their mixtures can serve as lipophilic compound. Illustrative suitable alcohols are ethanol, n-propanol and isopropanol, while suitable esters are ethyl acetate, butyl acetate, ethyl laurate, methyl propionate and isopropyl myristate. As used herein, the term "aliphatic alcohol" includes polyols such as glycerol, propylene glycol and polyethylene glycols. A mixture of alcohol and ester is preferred, and in particular, a mixture of ethanol and ethyl laurate myristate is most preferred.

The concentration of lipophilic compound required necessarily varies according to other factors such as the desired semi-solid consistency and the desired skin penetration promoting effects. The preferred topical composition contains lipophilic compound in the range of 7 percent to 40 percent by weight based on the total weight of the composition. Where a mixture of aliphatic alcohol and aliphatic ester are employed, the preferred amount of alcohol is in the range of 5 percent to 15 percent, while that of aliphatic ester is in the range from 2 percent to 15 percent (again based on the total weight of the composition).

An option, but preferred, component of the present invention is an emulsifier. Although not a critical factor, a suitable emulsifier generally will exhibit a hydrophilic-lipophilic balance number greater than 10. Sucrose esters, and specifically sucrose stearate, can serve as emulsifiers for the topical composition of the present invention. Sucrose stearate is a well known emulsifier available from various commercial sources. When an emulsifier is used, sucrose stearate present up to about 2 percent, based on the total weight of the composition, is preferred. The preferred amount of sucrose stearate emulsifier can also be expressed as a weight ratio of emulsifier to polysaccharide gum. A ratio of 1 to 6 emulsifier to gum is preferred, and a ratio of 1 to 4 is most preferred to generate the desired semi-solid consistency and separation resistance.

The present invention includes an acid buffer system. Acid buffer systems serve to maintain or buffer the pH of compositions within a desired range. The term "buffer system" or "buffer" as used herein has reference to a solute agent or agents which, when in a water solution, stabilize such solution against a major change in pH (or hydrogen ion concentration or activity) when acids or bases are added thereto. Solute agent or agents which are thus responsible for a resistance to change in pH from a starting buffered pH value in the range indicated above are well known. While their are countless suitable buffers, potassium phosphate monohydrate has proven effective for compositions of the present invention.

The final pH value of the pharmaceutical composition of the present invention may vary within the physiologically compatible range. Necessarily, the final pH value is not irritating to human skin. Without violating this constraint, the pH may be selected to improve prostaglandin $E_1$ stability and to adjust consistency when required. With these factors accounted for, the preferred pH value is about 3.0 to 7.4. The most preferred pH range is from about 3.5 to about 6.0.

The remaining component of the composition is water, which is necessarily purified. The composition contains water in the range of about 50 to about 90 percent, based on the total weight of the composition. The specific amount of water present is not critical, however, being adjustable to obtain the desired consistency and/or concentration of the other components.

Additionally, known transdermal penetration enhancers can also be added, if desired. Illustrative are dimethyl sulfoxide (DMSO), dimethyl acetamide (DMA), 2-pyrrolidone, N,N-diethyl-m-toluamide (DEET), 1-dodecylazacycloheptane-2-one (Azone®, a registered trademark of Nelson Research), N,N-dimethylformamide, N-methyl-2-pyrrolidone, calcium thioglycolate, oxazolidinone, dioxolane derivatives, laurocapram derivatives, and macrocyclic enhancers such as macrocyclic ketones.

Prostaglandin $E_1$ stabilizers, coloring agents, rheological agents, and preservatives can be added to the extent that they do not overly limit prostaglandin $E_1$ skin penetration or prevent the desired semi-solid consistency.

Contemplated dosage forms of the semi-solid pharmaceutical composition of the present invention are creams, gels, and the like, also including but not limited to compositions suitable for use with transdermal patches and like devices.

The ingredients listed above may be combined in any order and manner that produces a stable composition comprising a prostaglandin $E_1$ evenly dispersed throughout a semi-solid formulation. One available approach to preparing such compositions involves evenly dispersing the polysaccharide gum (or polyacrylic acid) in a premixed water/buffer solution and then thoroughly homogenizing (i.e. mixing) the resulting mixture, which will be labelled "Part A." When present, the emulsifier is added to the water/buffer solution before dispersing the polysaccharide gum. Any suitable method of adjusting the pH value of Part A to the desired level may be used, for example, by adding concentrated phosphoric acid or sodium hydroxide.

Separately, the prostaglandin $E_1$ is dissolved with agitation in the lipophilic compound, which itself may be a mixture of alcohols, esters, or alcohol with ester. Next, the penetration enhancer is added. Alternatively, when the lipophilic compound includes both an alcohol and an ester, the prostaglandin $E_1$ can be dissolved in the alcohol before adding the penetration enhancer followed by the ester. In either case, the resulting mixture will be labelled "Part B." The final step involves slow addition (.e.g. dropwise) of Part B into Part A under constant mixing.

The resulting topical composition, when compared to exhibits the advantageous properties described above, including improved prostaglandin $E_1$ permeation and bioavailability without drug overloading, reduced skin damage and related inflammation, and increased flexibility in design of dosage forms. These compositions can be used for prolonged treatment of peripheral vascular disease, male impotency and other disorders treated by prostaglandin $E_1$, while avoiding the low bioavailability and rapid chemical decomposition associated with other delivery methods. Application of prostaglandin $E_1$ in a topical composition of the present invention to the skin of a patient allows a predetermined amount of prostaglandin $E_1$ to be administered continuously to the patient and avoids undesirable effects present with a single or multiple administrations of larger dosages by injection. By maintaining a sustained dosage rate, the prostaglandin $E_1$ level in the patient's target tissue can be better maintained within the optimal therapeutic range.

The practice of the present invention is demonstrated in the following examples. These examples are meant to illustrate the invention rather than to limit its scope. Variations in the treating compositions which do not adversely affect the effectiveness of prostaglandin $E_1$ will be evident to one skilled in the art, and are within the scope of this invention. For example, additional ingredients such as coloring agents, anti-microbial preservatives, emulsifiers, perfumes, prostaglandin $E_1$ stabilizers, and the like may be included in the compositions as long as the resulting composition retains desirable properties, as described above. Unless otherwise indicated, each composition is prepared by conventionally admixing the respective indicated components together.

EXAMPLE 1

Topical Prostaglandin $E_1$ Composition A

Composition A was prepared as follows. Part A was formed by dissolving 0.4 parts prostaglandin $E_1$ (Alprostadil USP) in 5 parts ethyl alcohol. Next, 5 parts dodecyl 2-(N, N-dimethylamino)-propionate were mixed into the alcohol-prostaglandin $E_1$ solution, followed by 5 parts ethyl laurate.

Part B was prepared starting from a pH 5.5 water/buffer solution. The water/buffer solution was prepared by adding sufficient potassium phosphate monohydried to purified water to create a 0.1 M solution. The pH of the water/buffer solution was adjusted to 5.5 with a strong base solution (1 N sodium hydroxide) and a strong acid (1 N phosphoric acid). The buffer solution represented about 80 parts of the total composition.

To the buffer solution, was added 0.5 parts ethyl laurate. Next, the locust bean gum (in powder form) was dispersed in the buffer solution and homogenized using a homogenizer. TABLE 1, below, contains a list of ingredients.

The resulting composition was a spreadable, semi-solid suitable for application to the skin without the need for supporting devices such as patches and adhesive strips. The composition was both homogenous in appearance and resistant to separation.

Composition A was evaluated for skin penetration using shed snake skin as a model barrier. Shed snake skin was obtained from the Animal Care Unit of the University of Kansas. With head and tail sections removed, the skin was randomly divided into test sections and then hydrated by soaking.

The samples were then evaluated using Franz-type Diffusion Cells (surface are 1.8 cm$^2$). Specifically, skin pieces were mounted on top of a receptor cell of a vertical diffusion cell assembly in which a small magnetic bar was inserted and filled with an isotonic buffer. A seal was placed on top of the skin section followed by a donor cell. The two cells were clamped together. Known amounts of the formulations were applied on the bottom of a small capped vial (weight ≈5 grams) which fits exactly to the donor cell to ensure uniform distribution. The vials were placed on the skin in the donor cell. To reduce the evaporation of the ingredients, the donor cell and vial were gently taped together with a water-resistant adhesive band. The cells were transferred to a stirred water bath (32° C.). Samples were withdrawn from the cells each hour for four hours and analyzed for the concentration of prostaglandin $E_1$, with changes in concentration indicating the amount penetrating. Tests with multiple skin samples yielded data that were averaged.

For a discussion of the use of shed snake skin in the evaluation of drug penetration, see U.S. Pat. No. 4,771,004 to Higuchi, which is incorporated here by reference to the extent that it is not inconsistent.

The prostaglandin $E_1$ penetrated quickly at a relatively sustained rate for four hours. The results of the penetration study are presented in TABLE 2, below, and in FIG. 1.

EXAMPLE 2

Topical Prostaglandin $E_1$ Composition B

Composition B was prepared using the ingredients listed in TABLE 1, below. Composition B contained more prostaglandin $E_1$ than Composition A. Despite this increased drug loading, Composition B exhibited a similar semi-solid consistency and homogenous appearance. The penetration of prostaglandin $E_1$ was measured according to the technique described in Example 1. Composition B provided a relatively fast, sustained delivery of prostaglandin $E_1$. The results are presented in TABLE 2, below, and in FIG. 1.

EXAMPLE 3

Topical Prostaglandin $E_1$ Composition C

Composition C was prepared using the ingredients listed in TABLE 1, below. Composition B contained more prostaglandin $E_1$ than either Composition A or B. The increased drug loading had little or no effect on the consistency or appearance, which substantially matched that of Compositions A and B. The penetration of prostaglandin $E_1$ was again measured according to the technique described in Example 1. According to this test, Composition C also provided a relatively fast, sustained delivery of prostaglandin $E_1$. The results are presented in TABLE 2, below, and in FIG. 1.

EXAMPLE 4

Topical Prostaglandin $E_1$ Composition D

Composition D was prepared using the ingredients listed in TABLE 1, below. The level of prostaglandin $E_1$ was again increased without substantially affecting the favorable consistency and separation resistance. The penetration of prostaglandin $E_1$ was again measured according to the technique described in Example 1. The results are presented in TABLE 2, below, and in FIG. 1.

EXAMPLE 5

Topical Prostaglandin $E_1$ Composition E

Composition E was prepared using the ingredients listed in TABLE 1, below. To assess the repeatability of compositions according to the present invention, the recipe of Composition D was again applied for Composition E. Repeatability was substantially confirmed by Composition E's favorable, semi-solid consistency and separation resistance. The penetration of prostaglandin $E_1$ was again measured according to the technique described in Example 1. The prostaglandin $E_1$ delivery from Composition E was again relatively fast and sustained. The results are presented in TABLE 2, below, and in FIG. 1.

EXAMPLE 6

Topical Prostaglandin $E_1$ Composition F

The level of prostaglandin $E_1$ was again increased for Composition F. The specific ingredients are listed in TABLE 1. The favorable consistency and separation resistance was undiminished. The results of a penetration analysis are presented in TABLE 2, below, and in FIG. 1.

EXAMPLE 7

Topical Prostaglandin $E_1$ Composition G

Composition G was prepared using the ingredients listed in TABLE 1. For Composition G, the recipe of Composition F was repeated except that the ester component (ester laurate) was omitted and the level of ethanol was increased a corresponding amount. The resulting composition was also a spreadable, semi-solid having a homogenous appearance and resistance to separation. The results of a penetration analysis are presented in TABLE 2, below, and in FIG. 1. While still favorable, these results reflect the relative benefit to compositions of the present invention from a lipophilic compound that includes both an ester component and an alcohol component.

TABLE 1

Topical Prostaglandin $E_1$ Compositions

| | Ingredient (wt %) | A | B | C | D | E | F | G |
|---|---|---|---|---|---|---|---|---|
| Part A: | prehydrated locust bean gum | 3 | 3 | 3 | 3 | 3 | 3 | 3 |
| | water/buffer (pH 55) | 81 | 81 | 81 | 81 | 81 | 81 | 81 |
| | sucrose stearate | 0.5 | 0.5 | 0.5 | 0.5 | 0.5 | 0.5 | 0.5 |
| Part B: | prostaglandin $E_1$ | 0.1 | 0.2 | 0.3 | 0.4 | 0.4 | 0.5 | 0.4 |
| | DDAIP | 5 | 5 | 5 | 5 | 5 | 5 | 5 |
| | ethanol | 5 | 5 | 5 | 5 | 5 | 5 | 10 |
| | ethyl laurate | 5 | 5 | 5 | 5 | 5 | 5 | — |

EXAMPLE 8

Comparison of Penetration Profiles

TABLE 2 shows the cumulative amount of prostaglandin $E_1$ penetrating each hour for 4 hours for each example composition according to the present invention. These data demonstrate the ability of the present invention to delivery prostaglandin $E_1$ drugs transdermally.

FIG. 1 is graph generated from the data presented in TABLE 1. Significantly, and well represented in graphical form, compositions according to the present invention deliver effective skin penetration relatively fast and at a sustained rate. As expected, cumulative penetration increases with increased prostaglandin $E_1$ loading of the source composition.

TABLE 2

Cumulative Prostaglandin $E_1$ Penetration ($\mu g/cm^2$)

| Hour | A | B | C | D | E | F | G |
|---|---|---|---|---|---|---|---|
| 1 | 1.96 | 3.37 | 5.47 | 7.20 | 7.09 | 10.38 | 3.03 |
| 2 | 5.49 | 9.72 | 18.06 | 21.26 | 16.6 | 25.03 | 8.17 |
| 3 | 11.25 | 18.18 | 30.34 | 35.53 | 28.24 | 42.18 | 12.93 |
| 4 | 13.98 | 23.48 | 38.49 | 47.98 | 41.1 | 52.13 | 18.71 |

To further asses the effectiveness of compositions according the present invention, comparative example compositions were prepared. A first comparative example (Comparative Example 1) was prepared with the same recipe as Compositions D and E except that the DDAIP penetration enhancer was omitted. For A second comparative example (Comparative Example 2), the DDAIP was again omitted, but the level of ethanol was increased a corresponding amount. The specific ingredients used are listed in TABLE 3, below.

TABLE 3

Comparative Examples

| | Ingredient (wt %) | Comparative Composition 1 | Comparative Composition 2 |
|---|---|---|---|
| Part A: | prehydrated locust bean gum | 3 | 3 |
| | water/buffer (pH 5.5) | 86 | 81 |
| | sucrose stearate | 0.5 | 0.5 |
| Part B: | prostaglandin $E_1$ | 0.4 | 0.4 |
| | ethanol | 5 | 10 |
| | ethyl laurate | 5 | 5 |

The penetration of prostaglandin $E_1$ from was evaluated according to the technique described in Example 1. The results are presented in TABLE 4, below.

TABLE 4

Comparative Examples
Cumulative Prostaglandin $E_1$ Penetration ($\mu g/cm^2$)

| Hour | Comparative Composition 1 | Comparative Composition 2 |
|---|---|---|
| 1 | 2.64 | 1.55 |
| 2 | 4.46 | 3.69 |
| 3 | 6.59 | 6.63 |
| 4 | 9.67 | 11.05 |

The data of TABLE 4 are compared graphically to the example compositions having the same prostaglandin $E_1$ loading, Compositions D and E. The penetration data demonstrate that compositions according to the present invention benefit greatly from the presence of the DDAIP penetration enhancer.

The foregoing specification is intended as illustrative and is not to be taken as limiting. Still other variations within the spirit and the scope of the invention are possible and will readily present themselves to those skilled in the art.

We claim:

1. A topical composition which comprises:
   prostaglandin $E_1$;
   a skin penetration enhancer selected from the group consisting of an alkyl-2-(N,N-disubstituted amino)-alkanoate, an (N,N-disubstituted)-alkanol alkanoate, and a mixture thereof;
   a polysaccharide gum;
   a lipophilic compound selected from the group consisting of an aliphatic $C_1$ to $C_8$ alcohol, an aliphatic $C_8$ to $C_{30}$ ester, and a mixture thereof; and
   an acidic buffer system capable of providing a buffered pH value for said composition in the range of about 3 to about 7.4.

2. A topical composition which comprises:
   prostaglandin $E_1$;
   a skin penetration enhancer represented by the formula:

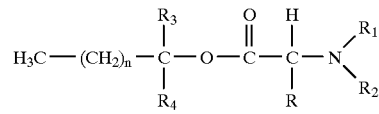

wherein n is an integer having a value in the range of about 4 to about 18; R is selected from the group consisting of hydrogen, $C_1$ to $C_7$ alkyl, benzyl and phenyl; $R_1$ and $R_2$ are selected from the group consisting of hydrogen and $C_1$ to $C_7$ alkyl; and $R_3$ and $R_4$ are selected from the group consisting of hydrogen, methyl and ethyl;
   a polysaccharide gum;
   a lipophilic compound selected from the group consisting of an aliphatic $C_1$ to $C_8$ alcohol, an aliphatic $C_8$ to $C_{30}$ ester, and a mixture thereof; and
   an acidic buffer system capable of providing a buffered pH value for said composition in the range of about 3 to about 7.4.

3. The topical composition in accordance with claim 1 wherein said penetration enhancer is a $C_4$ to $C_{18}$ alkyl (N,N-disubstituted amino)-acetate.

4. The topical composition in accordance with claim 1 wherein said penetration enhancer is a dodecyl (N,N-dimethylamino)-acetate.

5. The topical composition in accordance with claim 1 wherein said penetration enhancer is a dodecyl 2-(N,N-dimethylamino)-propionate.

6. A topical composition which comprises:
   prostaglandin $E_1$;
   a skin penetration enhancer represented by the formula:

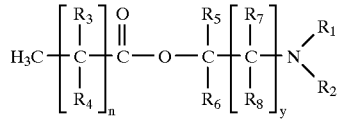

wherein n is an integer having a value in the range of about 5 to about 18; y is an integer having a value in the range of 0 to about 5; and $R_1$, $R_2$, $R_3$, $R_4$, $R_5$, $R_6$, and $R_7$ are selected from the group consisting of hydrogen, $C_1$ to $C_8$ alkyl, and $C_1$ to $C_8$ aryl; and $R_8$ is selected from the group consisting of hydrogen, hydroxyl, $C_1$ to $C_8$ alkyl, and $C_1$ to $C_8$ aryl;
   a polysaccharide gum;
   a lipophilic compound selected from the group consisting of an aliphatic $C_1$ to $C_8$ alcohol, an aliphatic $C_8$ to $C_{30}$ ester, and a mixture thereof; and
   an acidic buffer system capable of providing a buffered pH value for said composition in the range of about 3 to about 7.4.

7. The topical composition in accordance with claim 1 wherein said penetration enhancer is a $C_5$ to $C_{18}$ carboxylic acid ester.

8. The topical composition in accordance with claim 1 wherein said penetration enhancer is a 1-(N,N-dimethylamino)-2-propanol dodecanoate.

9. The topical composition in accordance with claim 1 wherein said penetration enhancer is a 1-(N,N-dimethylamino)-2-propanol myristate.

10. The topical composition in accordance with claim 1 wherein said penetration enhancer is a 1-(N,N-dimethylamino)-2-propanol oleate.

11. The topical composition in accordance with claim 1 wherein said polysaccharide gum is a galactomannan gum.

12. The topical composition in accordance with claim 11 wherein said galactomannan gum is a locust bean gum.

13. The topical composition in accordance with claim 11 wherein said galactomannan gum is a guar gum.

14. The topical composition in accordance with claim 1 wherein said lipophilic compound is ethanol.

15. The topical composition in accordance with claim 1 wherein said lipophilic compound is a polyol aliphatic alcohol.

16. The topical composition in accordance with claim 1 wherein said lipophilic compound is isopropyl myristate.

17. The topical composition in accordance with claim 1 wherein said lipophilic compound is ethyl laurate.

18. The topical composition in accordance with claim 1 wherein said lipophilic compound is a mixture of ethanol and isopropyl myristate.

19. The topical composition in accordance with claim 1 wherein said lipophilic compound is a mixture of ethanol and ethyl laurate.

20. The topical composition in accordance with claim 1 wherein said penetration enhancer is a dodecyl 2-(N,N-dimethylamino)-propionate, said polysaccharide gum is a locust bean gum, and said lipophilic compound is a mixture of ethanol and ethyl laurate.

21. A topical composition in accordance with claim 1 wherein said polysaccharide gum is 0.5 to 5 weight percent locust bean gum, said penetration enhancer is 0.5 to 25 weight percent dodecyl 2-(N,N-dimethylamino)-propionate, and said lipophilic compound is a mixture of 0.5 to 80 weight percent ethanol and 0.5 to 80 weight percent ethyl laurate, based on the total weight of the composition.

22. A topical composition in accordance with claim 1 wherein said polysaccharide gum is 0.5 to 5 weight percent locust bean gum, said penetration enhancer is 0.5 to 5 weight percent dodecyl 2-(N,N-dimethylamino)-propionate, and said lipophilic compound is a mixture of 0.5 to 25 weight percent ethanol and 0.5 to 25 weight percent ethyl laurate, based on the total weight of the composition.

23. A topical composition in accordance with claim 1, which further contains an emulsifier.

24. A topical composition in accordance with claim 23 wherein said emulsifier is an sucrose ester.

25. A topical composition in accordance with claim 23 wherein said emulsifier is sucrose stearate.

26. A topical prostaglandin composition which comprises:

prostaglandin $E_1$;

a skin penetration enhancer selected from the group consisting of an alkyl-2-(N,N-disubstituted amino)-alkanoate, an (N,N-disubstituted)-alkanol alkanoate, and a mixture thereof;

a polyacrylic acid polymer;

a lipophilic compound selected from of the group consisting of an aliphatic $C_1$ to $C_8$ alcohol, an aliphatic $C_8$ to $C_{30}$ ester, and a mixture thereof; and an acidic buffer system capable of providing a buffered pH value for said composition in the range of about 3 to about 7.4.

27. A topical composition in accordance with claim 26 wherein said polyacrylic acid polymer is a carbomer.

* * * * *

UNITED STATES PATENT AND TRADEMARK OFFICE
CERTIFICATE OF CORRECTION

PATENT NO. : 6,046,244
DATED : April 4, 2000
INVENTOR(S) : Servet Büyüktimkin

It is certified that error appears in the above-identified patent and that said Letters Patent is hereby corrected as shown below:

Col. 5, line 44, "(1→6)" should be -- (1→4) --.
Col. 10, line 44, "(pH 55)" should be -- (pH 5.5) --.

Signed and Sealed this

Twenty-seventh Day of March, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.    : 6,046,244
DATED         : April 4, 2000
INVENTOR(S)   : Servet Büyüktimkin Page 1 of 1

It is certified that error appears in the above-identified patent and that said Letters Patent is hereby corrected as shown below:

Column 6,
Line 1, "represent" should be -- present --.
Line 31, after "as" insert -- a --.
Line 51, "option" should be -- optional --.

Column 7,
Line 9, "their" should be -- there --.

Column 8,
Line 1, after "topical" delete "composition, when compared to" and insert
-- composition --.
Line 46, "monohydried" should be -- monohydride --.

Column 10,
Line 62, "1" should be -- 2 --.

Column 11,
Line 11, "asses" should be -- assess --.
Line 17, "A" should e -- a --.
Line 66, (claim 1), "(N,N-disubstituted)-alkanol" should
be --(N,N-disubstituted amino)-alkanol --.

Column 14,
Line 24 (claim 26), "N,N-disubstituted)-alkanol" should be
--(N,N-disubstituted amino)-alkanol --.

Signed and Sealed this

Thirteenth Day of November, 2001

Attest:

*Nicholas P. Godici*

NICHOLAS P. GODICI
*Attesting Officer*  *Acting Director of the United States Patent and Trademark Office*